US009198625B2

(12) United States Patent
Tsukagoshi

(10) Patent No.: US 9,198,625 B2
(45) Date of Patent: Dec. 1, 2015

(54) MEDICAL IMAGING APPARATUS AND MEDICAL IMAGING METHOD

(75) Inventor: Shinsuke Tsukagoshi, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 538 days.

(21) Appl. No.: 12/772,378

(22) Filed: May 3, 2010

(65) Prior Publication Data

US 2010/0292570 A1      Nov. 18, 2010

(30) Foreign Application Priority Data

May 18, 2009      (JP) .................................. 2009-120119

(51) Int. Cl.
*A61B 6/06* (2006.01)
*A61B 6/03* (2006.01)
*A61B 6/00* (2006.01)
*A61M 5/00* (2006.01)
*A61M 5/48* (2006.01)

(52) U.S. Cl.
CPC .................. *A61B 6/032* (2013.01); *A61B 6/481* (2013.01); *A61B 6/488* (2013.01); *A61B 6/504* (2013.01); *A61M 5/007* (2013.01); *A61M 5/482* (2013.01)

(58) Field of Classification Search
CPC ........ A61B 6/032; A61B 6/481; A61B 6/488; A61B 6/504; A61M 5/007; A61M 5/482
USPC ........................ 600/407, 424, 431; 378/1–120
See application file for complete search history.

(56) References Cited

U.S. PATENT DOCUMENTS

| 2007/0078330 | A1* | 4/2007 | Haras et al. ................... 600/407 |
| 2008/0119715 | A1* | 5/2008 | Gonzalez Molezzi et al. ............................ 600/407 |

FOREIGN PATENT DOCUMENTS

| CN | 1706344 A | 12/2005 |
| CN | 101185591 A | 5/2008 |
| JP | 1-207038 A | 8/1989 |
| JP | 2001-149380 A | 6/2001 |
| JP | 2006-141497 | 6/2006 |
| JP | 2006-518649 | 8/2006 |
| JP | 2007-021006 | 2/2007 |
| JP | 2007-143880 | 6/2007 |
| JP | 2007-275360 | 10/2007 |
| JP | 2008-126072 A | 6/2008 |

OTHER PUBLICATIONS

Translation of Japanese Publication 2007-143880, Jun. 14, 2007.*
Office Action issued Nov. 30, 2011, in Chinese Patent Application No. 201010182931.X.

(Continued)

*Primary Examiner* — Mark Remaly
(74) *Attorney, Agent, or Firm* — Oblon, McClelland, Maier & Neustadt, L.L.P.

(57) ABSTRACT

An injection part injects a contrast agent into a subject. An image acquiring part images the subject with the contrast agent injected, and acquires a plurality of image data with different imaging times. A pixel value calculator obtains a pixel value within a region of interest set in each of the image data acquired by the image acquiring part, for each of the image data. An injection controller controls injection of the contrast agent by the injection part in accordance with the pixel value obtained for each of the image data.

15 Claims, 6 Drawing Sheets

(56) References Cited

OTHER PUBLICATIONS

Office Action issued Aug. 20, 2013 in Japanese Patent Application No. 2009-120119 filed May 18, 2009.

Office Action issued Jun. 17, 2014 in Japanese Patent Application No. 2013-157152.

Office Action issued May 28, 2013, in Japanese Application No. 2009-120119.

* cited by examiner

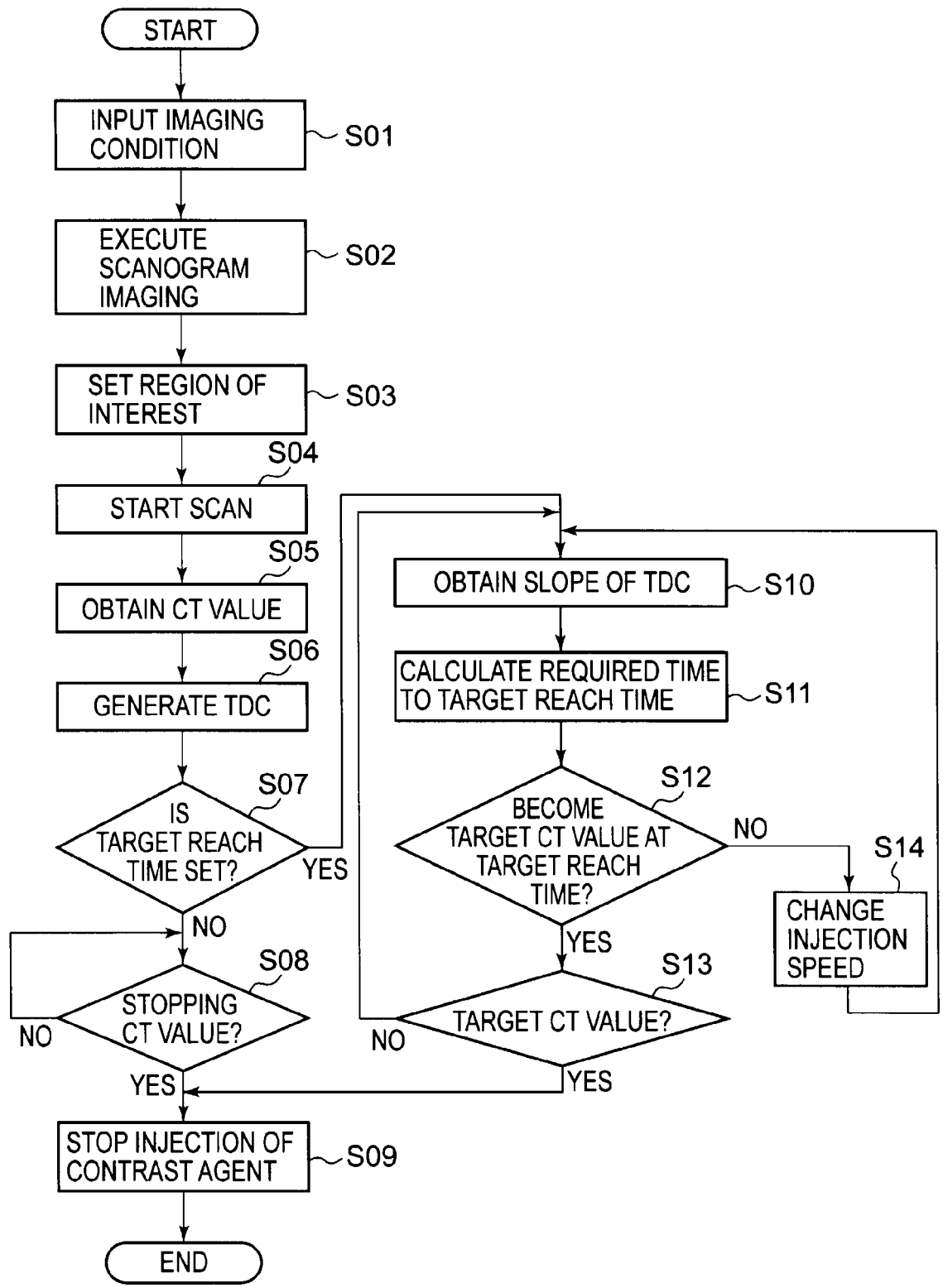

MEDICAL IMAGING APPARATUS AND MEDICAL IMAGING METHOD

BACKGROUND OF THE INVENTION

1. Field of the Invention

The present invention relates to a medical imaging apparatus and medical imaging method for imaging in a state that a contrast agent is injected into a subject.

2. Description of the Related Art

An example of a method for locating a lesion in a blood vessel or a lesion in an organ around a blood vessel is CTA (Computed Tomography Angiography). Such a lesion is aneurysm, vascular occlusion, or the like. An image obtained by a general X-ray CT (Computed Tomography) apparatus is low-contrast because the X-ray absorption value in a soft tissue such as an organ and a blood vessel is small in the image. Therefore, it is difficult to make a sufficient diagnosis of the soft tissue by the image obtained by the general X-ray CT apparatus. In contrast, CTA is a method of injecting a contrast agent with a high X-ray absorption value into a subject and imaging in a state that the X-ray absorption value in a focused blood vessel is increased. By employing CTA, it is possible to increase contrast and obtain a clear image of the organ.

There is a technique of determining the timing to start imaging by an X-ray CT apparatus in accordance with the concentration of a contrast agent injected into a subject (refer to Japanese Unexamined Patent Application Publication No. 2007-143880). In this technique, the contrast agent is injected into the subject by a contrast agent injector, and the concentration of the contrast agent in a region of interest (ROI) is monitored. When the concentration of the contrast agent in the ROI exceeds a threshold, the X-ray CT apparatus automatically starts imaging. This technique enables an operator to cause the imaging apparatus to determine the timing of imaging in accordance with the concentration of the contrast agent and to automatically start imaging, only by giving an instruction to start imaging to the imaging apparatus.

With reference to FIG. 1, the timing to start imaging according to a conventional technique will be described. FIG. 1 is a view for describing the timing to start imaging, and is a graph showing change in concentration of a contrast agent in an ROI of a subject.

The contrast agent injected into the subject moves in the subject on a blood flow and reaches a target organ. In imaging by the X-ray CT apparatus, the timing of flow of the contrast agent into the target organ is determined to start a scan (may be referred to as the "main scan" hereinafter) and acquire image data.

In the conventional technique, a scan called a prep scan may be executed before the main scan. The prep scan is a scan for observing change in concentration of the contrast agent in the ROI of the subject with the contrast agent injected. The prep scan is a scan method of performing image reconstruction while collecting X-ray projection data of the subject, and generating image data in real time while scanning.

The concentration of the contrast agent in the ROI is obtained based on the image data obtained by the prep scan and, at a point that the concentration of the contrast agent is increased to a certain extent, the prep scan is stopped and the main scan is automatically started. In this case, when the CT value (the concentration of the contrast agent) within the ROI becomes a threshold or more, the main scan is automatically started.

A curve showing temporal change in stain of a contrast agent is called a Time-Density Curve (referred to as the "TDC" hereinafter).

For example, a curve showing temporal change in CT value within the ROI shall be the TDC. When the contrast agent flows into a tissue, the CT value in the tissue is increased. Thus, the CT value represents the state of stain of the contrast agent.

FIG. 1 shows an example of the TDC. The horizontal axis takes time t, and the vertical axis takes CT values (pixel values). At a point immediately after injection of the contrast agent into the subject, the contrast agent is not yet flown into the ROI. Therefore, as shown by a TDC 500, the CT value within the ROI is low. After a lapse of time, the contrast agent flows into the ROI and the CT value changes. For example, the CT value increases. When the CT value in the ROI becomes a predetermined threshold or more, it is assumed that the contrast agent already flows into a target organ. Therefore, the main scan is started at this point. Since the CT value in the ROI becomes the threshold or more at a time $T_0$, the main scan is started at the time $T_0$.

Thus, the main scan is automatically started, and it becomes possible to start imaging at the timing that the contrast agent flows into the target organ. Then, by executing the main scan for a certain time having been set in advance, CT image data representing the target organ with the contrast agent injected is acquired. The main scan is executed from the time $T_0$ that the main scan starts to a time $T_1$ after a lapse of the certain time, and the main scan is ended at the time $T_1$.

However, in the method according to the conventional technique, only the timing to start injection of the contrast agent and the timing to start the main scan are controlled. In the conventional technique, during the main scan, the injection amount and injection pressure (injection speed) of the contrast agent are not controlled based on the TDC. Moreover, in the conventional technique, control of ending injection of the contrast agent in response to end of the main scan is not performed. For example, as shown in FIG. 1, injection of the contrast agent is still continued after the time $T_1$ that the main scan ends. Since injection of the contrast agent into the subject is continued though the main scan ends, the contrast agent is wastefully injected, and a burden is imposed on the patient.

The change in concentration of the contrast agent (the temporal change in CT value) largely varies depending on the weights of patients, diseases, and so on. To be specific, a time from start of injection of the contrast agent to flow of the contrast agent into the target organ varies depending on patients and the types of diseases. In the conventional technique, the injection amount and injection pressure of the contrast agent are not controlled during the main scan. Therefore, even when the main scan is started at the time $T_0$, the main scan may end before the contrast effect increases (the CT value increases), depending on patients and the types of diseases. In this case, the main scan cannot be executed with high contrast effect, and it is therefore difficult to acquire image data having a desired contrast. Since there is a need to perform imaging again in such a case, a burden is imposed on the patient.

SUMMARY OF THE INVENTION

An object of the present invention is to provide a medical imaging apparatus and medical imaging method that enable imaging at such timing that produces a desired contrast effect.

In a first aspect of the present invention, a medical imaging apparatus includes: an injection part configured to inject a contrast agent into a subject at a predetermined injection speed; an image acquiring part configured to image the subject with the contrast agent injected and acquire a plurality of image data with different imaging times; a pixel value calculator configured to obtain, for each of the image data, a pixel value within a region of interest set in each of the image data acquired by the image acquiring part; and an injection controller configured to control injection of the contrast agent by the injection part in accordance with the pixel value obtained for each of the image data.

According to the first aspect, control of injection of the contrast agent in accordance with the pixel value within the region of interest enables imaging at the timing that produces a desired contrast effect.

In a second aspect of the present invention, a medical imaging method includes: injecting a contrast agent into a subject at a predetermined injection speed; imaging the subject with the contrast agent injected to acquire a plurality of image data with different imaging times; obtaining, for each of the image data, a pixel value within a region of interest set in each of the image data; and controlling injection of the contrast agent in accordance with the pixel value obtained for each of the image data.

BRIEF DESCRIPTION OF THE DRAWINGS

FIG. 6 is a flow chart for describing the operation of the medical imaging apparatus according to the embodiment of the present invention.

DETAILED DESCRIPTION OF THE EMBODIMENTS

Figure 1:
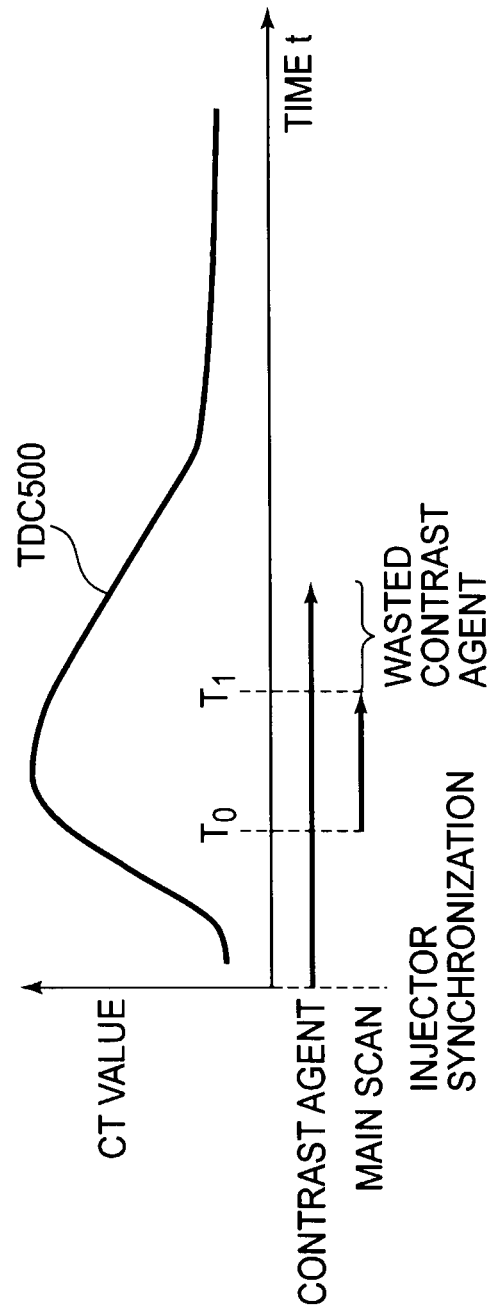
FIG. 1 is a view for describing the timing to start imaging in accordance with the concentration of a contrast agent in a conventional technique, and is a graph showing change in concentration of the contrast agent in a region of interest of a subject.
Figure 2:
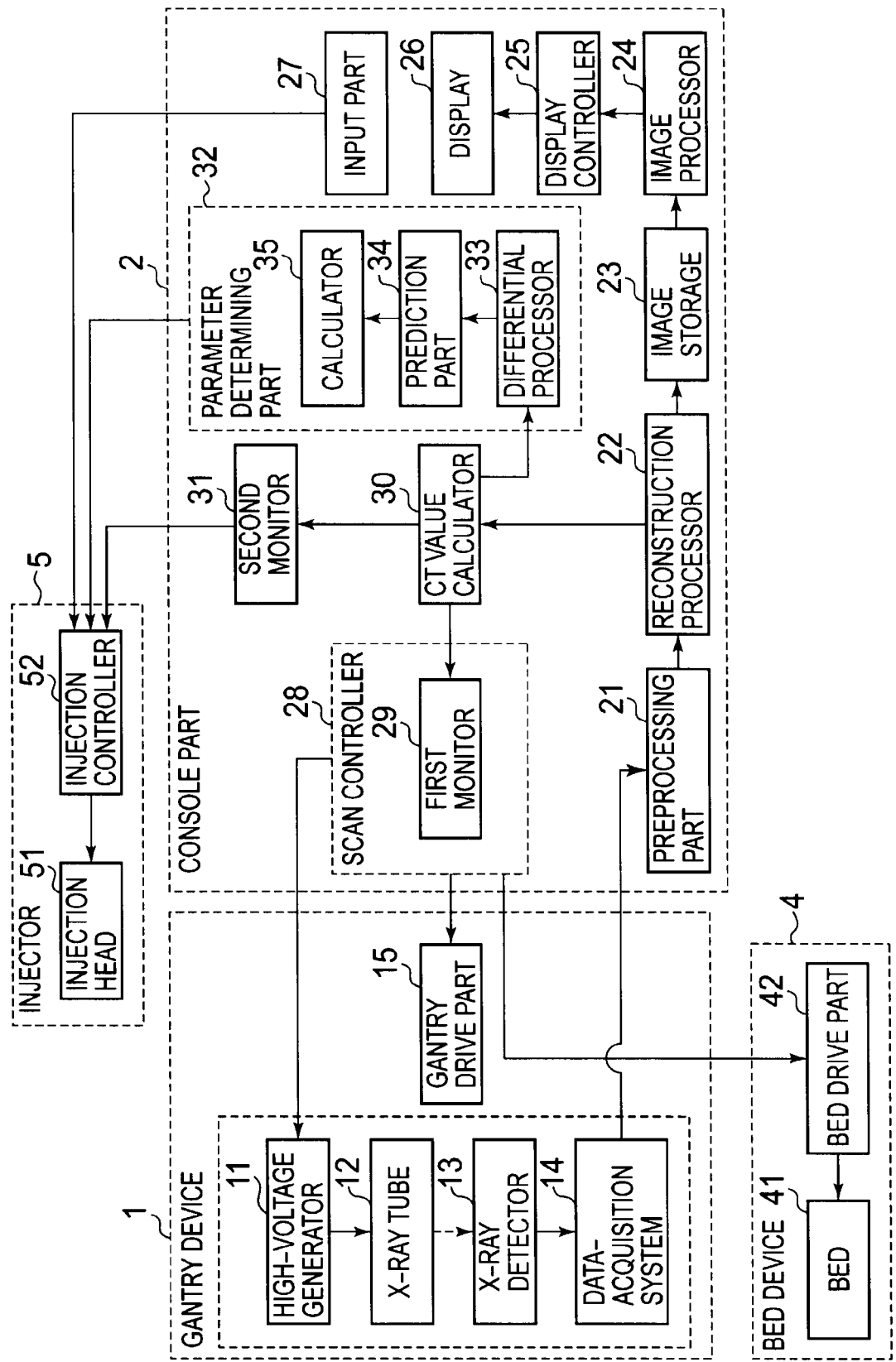
FIG. 2 is a block diagram showing a medical imaging apparatus according to an embodiment of the present invention.

With reference to FIG. 2, a medical imaging apparatus according to an embodiment of the present invention will be described.

The medical imaging apparatus according to this embodiment is provided with a gantry device 1, a console part 2, a bed device 4, and an injector 5. The gantry device 1, the console part 2 and the bed device 4 configure an X-ray CT apparatus.
(Injector 5)

The injector 5 automatically injects a contrast agent into a subject. The injector 5 is provided with an injection head 51 for injecting a contrast agent into a subject, and an injection controller 52 that controls the operation of the injection head 51. For example, the injection head 51 is provided with a cylinder for filling a contrast agent. The injection controller 52 controls the injection head 51 in accordance with injection conditions inputted through an input part 27.

The injection head 51 injects the contrast agent inside the cylinder into a subject by using power such as air pressure, motor or oil pressure in accordance with preset contrast conditions (the injection amount and injection pressure (injection speed) of the contrast agent).

As one example, the injection head 51 injects 100 ml of contrast agent in total into a subject at an injection speed (an injection pressure) of 3 ml/sec under control by the injection controller 52. The injection head 51 is equivalent to one example of the "injection part" of the present invention. The injection controller 52 is equivalent to one example of the "injection controller" of the present invention.
(X-ray CT Apparatus)

The gantry device 1 is provided with a rotating gantry that houses an X-ray tube 12 and an X-ray detector 13. The gantry device 1 collects X-ray projection data regarding a subject. The X-ray projection data is outputted to the console part 2 and used for a process such as an image reconstruction process. The X-ray CT apparatus is equivalent to one example of the "image acquiring part" of the present invention.

The gantry device 1 has the X-ray tube 12, and the X-ray detector 13 paired with the X-ray tube 12. The X-ray detector 13 is, for example, a detector in which 1000 channels of detection elements are arranged in a row. Alternatively, the X-ray detector 13 may be a two-dimensional X-ray detector. The two-dimensional X-ray detector is a detector in which a plurality of detection elements are arranged in two directions orthogonal to each other (a slice direction and a channel direction). A high-voltage generator 11 supplies, to the X-ray tube 12, a high voltage for emitting an X-ray in accordance with a control signal from a scan controller 28.

To the X-ray detector 13, a data acquisition system (DAS) 14 is connected. The DAS 14 has a plurality of data collection elements, as the X-ray detector 13 has the detection elements. The DAS 14 collects X-rays (detection signals) detected by the X-ray detector 13 so as to correspond to data collection control signals outputted from the scan controller 28. The collected data are equivalent to the X-ray projection data. The DAS 14 amplifies the signals outputted from the X-ray detector 13 and converts the amplified signals into digital signals.

The X-ray detector 13 detects the X-ray emitted from the X-ray tube 12 and transmitted through the subject. The DAS 14 amplifies the detection signals outputted from the X-ray detector 13 and converts the amplified detection signals into digital signals. The DAS 14 collects the signals after converted into digital signals as the X-ray projection data. The X-ray tube 12, an X-ray diaphragm that is not shown in the drawing, the X-ray detector 13, and the DAS 14 are integrally fixed to a gantry that is not shown in the drawing.

A gantry drive part 15 makes the rotating gantry that is not shown in the drawing rotate based on a gantry control signal outputted from the scan controller 28. Consequently, the rotating gantry is rotated about the rotation center.
(Console Part 2)

The console part 2 is provided with a preprocessing part 21, a reconstruction processor 22, an image storage 23, an image processor 24, a display controller 25, a display 26, an input part 27, a scan controller 28, a CT value calculator 30, a second monitor 31, and a parameter determining part 32.

The preprocessing part 21 executes a process such as sensitivity correction and X-ray intensity correction on the data outputted from the DAS 14. The preprocessing part 21 outputs the processed X-ray projection data to the reconstruction processor 22.

The reconstruction processor 22 generates image data by executing a back projection process on the X-ray projection data on which the preprocessing part 21 has executed sensitivity correction.

Consequently, image data representing a subject is generated.

The image data outputted from the reconstruction processor 22 is temporarily stored in the image storage 23.

The image processor 24 executes image processing on image data. For example, the image processor 24 executes image processing on image data in accordance with an operator's instruction inputted through the input part 27. As one example, the image processor 24 executes a volume rendering process to generate three-dimensional image data. The image processor 24 may execute an MPR (Multi Plannar Reconstruction) process to generate MPR image data (image data in an arbitrary cross section). The image processor 24 outputs the image data such as the three-dimensional image data and the MPR image data to the display controller 25. The display controller 25 controls the display 26 such as a liquid crystal display and a CRT to display an image based on the image data outputted from the image processor 24.

In order to make the rotating gantry rotate at a constant speed with stability, the scan controller 28 outputs a rotation control signal to the gantry drive part 15. Moreover, the scan controller 28 outputs an X-ray generation control signal for controlling generation of an X-ray, to the high-voltage generator 11. Moreover, the scan controller 28 outputs a detection control signal indicating the timing of detection of the X-ray, to the DAS 14.

The bed device 4 is provided with a bed 41 and a bed drive part 42. The bed 41 is provided with a bed top to place a subject and a bed base for supporting the bed top. The bed top can be moved by the bed drive part 42 in the body-axis direction of a subject (the slice direction). The bed base can move the bed top in the vertical direction by the bed drive part 42.

The input part 27 is an input device by which the operator inputs information such as conditions of a main scan or conditions of a prep scan.

The X-ray CT apparatus collects the X-ray projection data while making the rotating gantry rotate under control by the scan controller 28. For example, the X-ray CT apparatus executes a prep scan to determine the timing to start a main scan, and executes the main scan at appropriate timing.

Prior to execution of a scan, determination of imaging slice positions, and setting of prep scan conditions (a tube voltage, a tube current, a scan time, and so on), main scan conditions (a tube voltage, a tube current, a scan time, and so on) and prep conditions (conditions for start of the main scan, such as the threshold of the CT value) are performed. These conditions are stored into a storage, which is not shown in the drawing, included in the console part 2.

In execution of the prep scan, the prep scan is executed under control by the scan controller 28, in accordance with the prep scan conditions. Consequently, the X-ray tube 12 and the X-ray detector 13 continuously rotate around a subject, an X-ray is generated from the X-ray tube 12 in accordance with the prep scan conditions, and data collection is repeatedly performed.

While executing the prep scan, the scan controller 28 controls the reconstruction processor 22. The reconstruction processor 22 generates tomographic image data based on the X-ray projection data acquired in the prep scan, under control by the scan controller 28. The tomographic image data generated by execution of the prep scan may be referred to as "monitoring image data."

(CT Value Calculator 30)

The CT value calculator 30 receives the image data generated by the reconstruction processor 22. Based on the image data, the CT value calculator 30 obtains the CT values of a plurality of pixels included in a region of interest (ROI) set in advance. For example, the CT value calculator 30 obtains the sum of the CT values of a plurality of pixels included in the ROI. The CT value calculator 30 may obtain the average of the CT values of a plurality of pixels included in the ROI.

The CT value calculator 30 is equivalent to one example of the "pixel value calculator" of the present invention. In this embodiment, a CT value is obtained as one example of a pixel value. As another example, an SD (Standard Deviation) value of an image may be obtained as a pixel value.

The ROI is set at an arbitrary position on an image by the operator through the input part 27. For example, the display controller 25 controls the display 26 to display an image based on the image data generated by the reconstruction processor 22. The operator designates a desired region on the image displayed by the display 26, through the input part 27. For example, the operator designates a region including a site to observe, through the input part 27. The region designated by the operator is set into the CT value calculator 30 as the region of interest. The CT value calculator 30 obtains the CT values of the plurality of pixels included in the ROI. The CT values of the plurality of pixels included in the ROI may be abbreviated as "the CT value within the ROI."

For example, based on each monitoring image data sequentially obtained by executing the prep scan, the CT value calculator 30 obtains the CT values of a plurality of pixels included in an ROI set in advance, for each monitoring image data. That is to say, the CT value calculator 30 obtains the CT value within the ROI along the time series. The ROI set for the monitoring image data obtained by a prep scan will be referred to as a monitoring ROI. The CT value calculator 30 outputs the CT values of the plurality of pixels included in the monitoring ROI at each time, to a first monitor 29. The CT values of the plurality of pixels included in the monitoring ROI may be abbreviated as the CT value within the monitoring ROI.

The first monitor 29 compares the threshold set prior to the prep scan (the prep conditions) with the CT value within the monitoring ROI to determine whether the CT value within the monitoring ROI has become the threshold or more. The first monitor 29 determines the timing that the CT value within the monitoring ROI has become the threshold or more as the timing of start of the main scan. That is to say, in a case that the CT value within the monitoring ROI has become the threshold or more, it is thought that a contrast agent has flown into a target site. The scan controller 28 stops the prep scan to execute the main scan in accordance with the main scan conditions.

Under control by the scan controller 28, the X-ray CT apparatus continues execution of the main scan. The reconstruction processor 22 generates a plurality of image data along the time sequence, based on the X-ray projection data sequentially obtained by execution of the main scan. The reconstruction processor 22 sequentially outputs the plurality of image data to the CT value calculator 30. The CT value calculator 30 receives the plurality of image data obtained by execution of the main scan from the reconstruction processor 22, and obtains the CT value within the preset ROI, for each of the image data.

That is to say, the CT value calculator 30 obtains the CT value within the ROI along the time series. The CT value calculator 30 outputs the CT value within the ROI at each time to the second monitor 31 and the parameter determining part 32. The display controller 25 controls the display 26 to display an image based on the image data generated by the reconstruction processor 22.

In a case that the CT value within the monitoring ROI is less than the threshold, the scan controller 28 continues execution of the prep scan. Then, until the first monitor 29 determines that the CT value within the monitoring ROI has become the threshold or more, the scan controller 28 continues execution of the prep scan.

(Second Monitor 31)

The second monitor 31 receives the CT value within the ROI at each time from the CT value calculator 30 and, when the CT value becomes a threshold set in advance (a stopping CT value A) or more, outputs, to the injector 5, an instruction to stop injection of the contrast agent. This threshold (the stopping CT value A) is a value inputted in advance by the operator through the input part 27, and is stored in a storage that is not shown in the drawing. The stopping CT value A is equivalent to the "stopping threshold" of the present invention.

Figure 3:
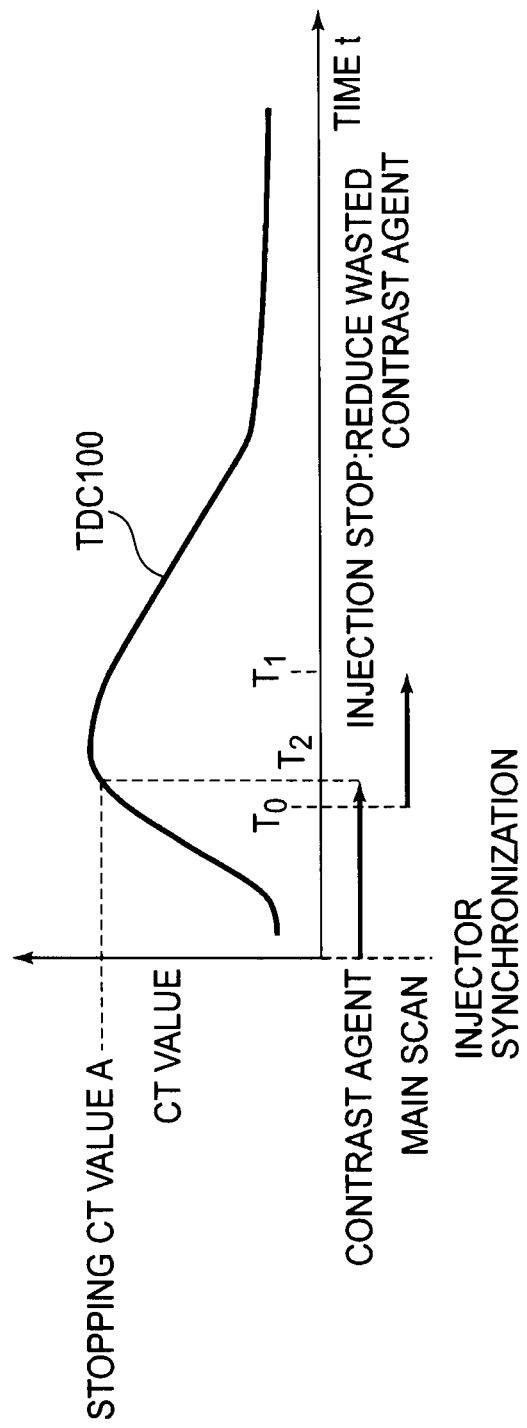
FIG. 3 is a view for describing the timing to start imaging and the timing to end imaging in accordance with the concentration of a contrast agent in the embodiment of the present invention, and is a graph showing change in concentration of the contrast agent in a region of interest of a subject.

FIG. 3 shows an example of a TDC. A TDC shows a temporal change of the CT value within the ROI. FIG. 3 is a view for describing the timing of start of imaging and the timing of end of imaging in accordance with the concentration of the contrast agent, and is a graph representing change in concentration of the contrast agent in the ROI of the subject. The horizontal axis takes time t, and the vertical axis takes CT values (pixel values). When the injector 5 injects the contrast agent into the subject, a change in concentration of the contrast agent in the ROI of the subject is obtained. A TDC 100 shows a temporal change of the CT value within the ROI. At a point immediately after injection of the contrast agent into the subject, the CT value within the ROI is low because the contrast agent has not flown into the ROI.

When the contrast agent has flown into the ROI and the CT value has become the threshold represented by the prep conditions or more, the scan controller 28 executes the main scan. At a time $T_0$, the CT value within the ROI becomes the threshold of the prep scan or more. Therefore, the scan controller 28 starts the main scan at time $T_0$.

When the CT value within the ROI becomes the stopping CT value A set in advance or more, the second monitor 31 outputs, to the injector 5, an instruction to stop injection of the contrast agent. At a time $T_2$ later than the time $T_0$, the CT value within the ROI becomes the stopping CT value A or more. Therefore, the second monitor 31 outputs an instruction to stop injection of the contrast agent to the injector 5 at the time $T_2$.

The injection controller 52 receives the instruction to stop injection of the contrast agent from the second monitor 31, and stops injection of the contrast agent into the subject by the injection head 51.

In this embodiment, the injection controller 52 stops injection of the contrast agent into the subject by the injection head 51 at the time $T_2$.

The scan controller 28 executes the main scan from the time $T_0$ when the main scan is started to a time $T_1$ after a lapse of a predetermined time. For example, the scan controller 28 ends the main scan at the time $T_1$, which is later than the time T2 when the CT value becomes the stopping CT value A. Thus, injection of the contrast agent by the injector 5 is stopped at the time $T_2$ during a period (from the time $T_0$ to the time $T_1$) when the main scan is executed. This makes it possible to reduce the wasted contrast agent while imaging with the contrast agent frown into the target site.

The second monitor 31 may detect a point that the amount of the contrast agent is saturated, based on the TDC 100. Upon detection of the point that the amount of the contrast agent is saturated, the second monitor 31 outputs the instruction to stop injection of the contrast agent to the injector 5. For example, the second monitor 31 differentiates the TDC 100 with respect to time, and obtains a point that the derivative becomes a preset threshold or less. The second monitor 31 regards the point that the derivative becomes the threshold or less as the point that the amount of the contrast agent is saturated.

The injection controller 52 receives the instruction to stop injection of the contrast agent and stops injection of the contract agent into the subject by the injection head 51.

Figure 4:
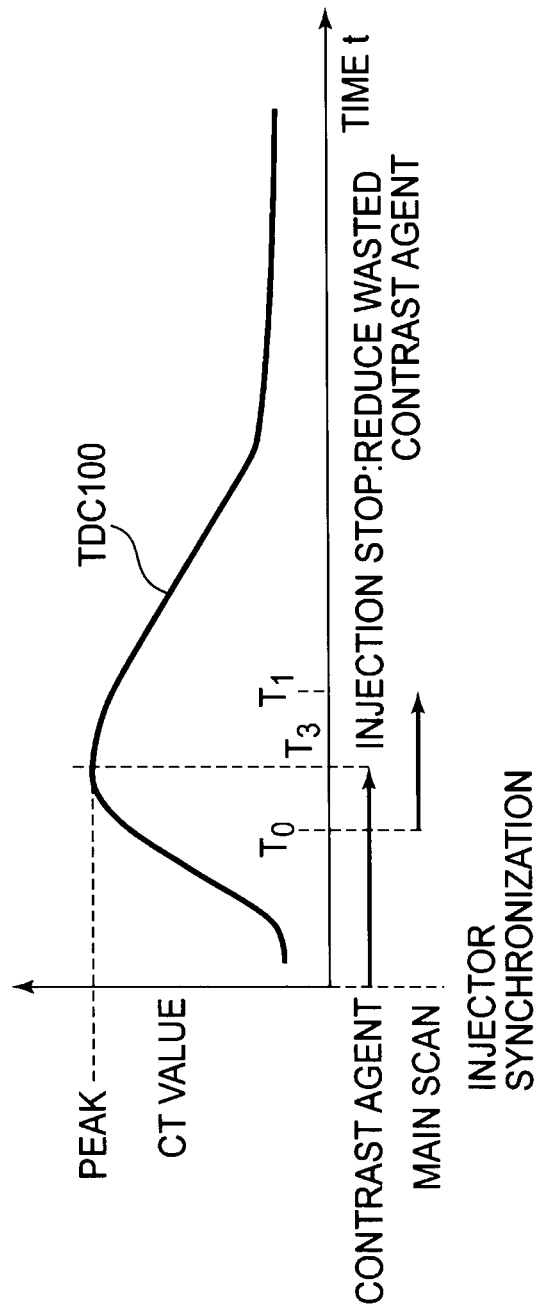
FIG. 4 is a view for describing the timing to start imaging and the timing to end imaging in accordance with the concentration of a contrast agent in the embodiment of the present invention, and is a graph showing change in concentration of the contrast agent in a region of interest of a subject.

As one example, the second monitor 31 may regard the peak point of the TDC 100 as the point that the amount of the contrast agent is saturated. In this case, when detecting the peak point of the TDC 100, the second monitor 31 outputs the instruction to stop injection of the contrast agent. With reference to FIG. 4, the peak point will be described. FIG. 4 is a view for describing the timing to start imaging and the timing to end imaging in accordance with the concentration of the contrast agent, and is a graph representing change in concentration of the contrast agent within the ROI of the subject. The horizontal axis takes time t, and the vertical axis takes CT values (pixel values).

The second monitor 31 receives the CT value within the ROI at each time from the CT value calculator 30 and differentiates the TDC 100 with respect to time, thereby obtaining a time $T_3$ that the TDC 100 forms the peak. When detecting the peak of the TDC 100, the second monitor 31 outputs, at the point, the instruction to stop injection of the contrast agent. The injection controller 52 receives the instruction to stop injection of the contrast agent from the second monitor 31, and stops injection of the contrast agent into the subject by the injection head 51.

The scan controller 28 executes the main scan from the time $T_0$ that the main scan is started to the time $T_1$ after a lapse of a predetermined time. The scan controller 28 ends the main scan at the time $T_1$, which is later than a time $T_3$ at the peak point. By stopping injection of the contrast agent at the point that the TDC 100 forms the peak, it is possible to reduce the wasted contrast agent while imaging in a state that the contrast agent has flown into a target site.

In this embodiment, injection of the contrast agent by the injector 5 may be stopped in accordance with the stopping CT value A, or injection of the contrast agent may be stopped at the point that the amount of the contrast agent is saturated. For example, injection of the contrast agent may be stopped at the point that the TDC 100 forms the peak point.

(Parameter Determining Part 32)

The parameter determining part 32 is provided with a differential processor 33, a prediction part 34, and a calculator 35. The parameter determining part 32 obtains an injection speed (an injection pressure) that enables the CT value within the ROI to reach a target CT value at a target reach time. The operator inputs, through the input part 27, a CT value for stopping injection of the contrast agent (the target CT value). Moreover, the operator inputs, through the input part 27, a time necessary for the CT value to reach the target CT value (the target reach time) from a point that injection of the contrast agent into the subject starts (the contrast starting point). The target CT value and the target reach time are values obtained from empirical rules. By injecting the contrast agent into the subject until the CT value within the ROI reaches the target CT value, a high contrast effect is obtained.

Consequently, it is possible to perform imaging at the timing with high contrast effect and acquire image data with high contrast effect.

The target CT value and target reach time inputted by the operator are stored into a storage, which is not shown in the drawing.

Under control by the injection controller 52, the injection head injects a predetermined injection amount (an initial value) of contrast agent into the subject at a predetermined injection speed (an initial value). As one example, the injection head 51 injects 100 ml (an initial value) of contrast agent in total into the subject at an injection speed (an injection pressure) of 3 ml/sec (an initial value). The target CT value is equivalent to one example of the "target pixel value" of the present invention. The target reach time is equivalent to one example of the "target reach time" of the present invention. The parameter determining part 32 is equivalent to one example of the "determining part" of the present invention.
(Differential Processor 33)

The differential processor 33 receives the CT value within the ROI at each time from the CT value calculator 30 and differentiates the TDC showing a temporal change of the CT value with respect to time, thereby obtaining the slope of the TDC at each time. That is to say, the differential processor 33 obtains the speed of stain of the contrast agent at each time.

Figure 5:
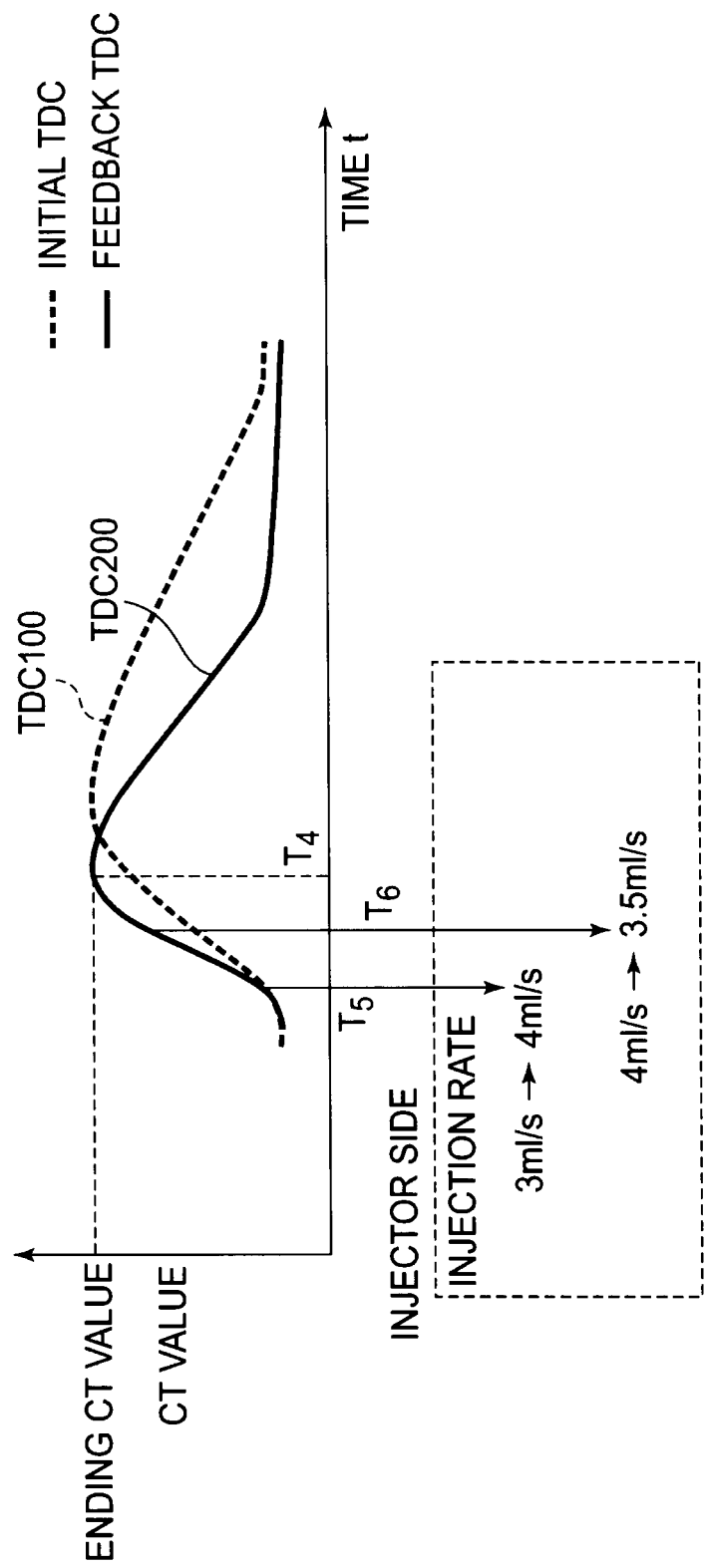
FIG. 5 is a view for describing a process for obtaining an injection speed in accordance with change in concentration of the contrast agent, and is a graph showing change in concentration of the contrast agent in a region of interest of a subject.

FIG. 5 shows one example of the TDC. FIG. 5 is a view for describing a process for obtaining an injection speed corresponding to a change in concentration of the contrast agent, and is a graph representing a change in concentration of the contrast agent in the ROI of the subject. The horizontal axis takes time t, and the vertical axis takes CT values (pixel values).

The TDC 100 is obtained when the contrast agent is injected into the subject at an injection speed (an injection pressure) of an initial value. The differential processor 33 receives the CT value within the ROI at each time from the CT value calculator 30 and differentiates the TDC 100 (the initial TDC indicated by a broken line) representing a temporal change of the CT value with respect to time, thereby obtaining the slope of the TDC 100 at each time. The differential processor 33 outputs information representing the slope of the TDC 100 at each time to the prediction part 34.
(Prediction Part 34)

The prediction part 34 receives the slope of the TDC at each time obtained by the differential processor 33. The prediction part 34 performs linear prediction based on the slope of the TDC at a latest time, the CT value at the latest time, and the target CT value. By the linear prediction, the prediction part 34 obtains a time taken for the CT value at the latest time to reach the target CT value. To be specific, the prediction part 34 obtains a difference between the target CT value and the CT value at the latest time (may be referred to as "the difference of the CT values" hereinafter). The prediction part 34 divides the difference of the CT values by the slope of the TDC at the latest time, thereby obtaining a time (may be referred to as the "prediction time" hereinafter) taken for the CT value at the latest time to reach the target CT value. The difference of the CT values is equivalent to one example of the "pixel value difference" of the present invention. The prediction time is equivalent to the "prediction time" of the present invention.

For example, a case that a time $T_4$ is set as the target reach time and an ending CT value E is set as the target CT value as shown in FIG. 5 will be described. The differential processor 33 obtains the slope of the TDC 100 at a latest time $T_5$. The prediction part 34 receives the slope of the TDC 100 at the time $T_5$, and performs linear presumption based on the slope of the TDC 100 at the time $T_5$, the CT value at the time $T_5$, and the ending CT value E (the target CT value). By the linear prediction, the prediction part 34 obtains a time taken for the CT value at the time $T_5$ to reach the ending CT value E (the target CT value). To be specific, the prediction part 34 obtains the difference (the difference of the CT values) between the ending CT value E (the target CT value) and the CT value at the latest time $T_5$. The prediction part 34 divides the difference of the CT values by the slope of the TDC 100 at the time $T_5$, thereby obtaining a time taken for the CT value at the time $T_5$ to reach the ending CT value E (the target CT value).
(Calculator 35)

The calculator 35 obtains a difference (may be referred to as "the time to the target reach time" hereinafter) between the aforementioned latest time and the target reach time. The calculator 35 determines whether the time to the target reach time and the prediction time obtained by the prediction part 34 coincide with each other. In a case that the time to the target reach time and the prediction time coincide with each other, it is predicted that injection of the contrast agent at the set injection speed will cause the CT value to reach the target CT value at the target reach time. In this case, injection of the contrast agent is continued at the set injection speed without change of the injection speed of the contrast agent. The time to the target reach time is equivalent to one example of the "temporal difference" of the present invention.

On the other hand, in a case that the time to the target reach time (the temporal difference) and the prediction time do not coincide with each other, it is predicted that injection of the contrast agent at the set injection speed will not cause the CT value to reach the target CT value at the target reach time. In this case, the calculator 35 obtains an injection speed for causing the CT value to reach the target CT value at the target reach time. To be specific, the calculator 35 divides the aforementioned difference of the CT values by the aforementioned time to the target reach time (the temporal difference) to obtain a new injection speed (injection pressure). The calculator 35 thus obtains an injection speed (an injection pressure) for causing the CT value to reach the target CT value at the target reach time.

In a case that the difference between the time to the target reach time (the temporal difference) and the prediction time is less than a certain time having been set in advance, it is predicted that injection of the contrast agent at the set injection speed will cause the CT value to reach substantially the target CT value at the target reach time. In this case, injection of the contrast agent may be continued at the set injection speed without change of the injection speed of the contrast agent. On the other hand, in a case that the difference between the time to the target reach time (the temporal difference) and the prediction time is the predetermined time or more, it is predicted that injection of the contrast agent at the set injection speed will not cause the CT value to reach a value close to the target CT value at the target reach time. In this case, the calculator 35 may divide the aforementioned difference of the CT values by the aforementioned time to the target reach time (the temporal difference) to obtain a new injection speed.

In the example shown in FIG. 5, the calculator 35 obtains the difference (the time to the target reach time) between the latest time $T_5$ and the time $T_4$ as the target reach time. The calculator 35 determines whether the time to the target reach time ($T_4$) and the prediction time obtained by the prediction part 34 coincide with each other. In a case that the time to the target reach time ($T_4$) and the prediction time do not coincide with each other, the calculator 35 divides the difference of the CT values (the difference between the ending CT value E and the CT value at the time $T_5$), by the time to the target reach time ($T_4$) (the difference between the time $T_5$ and the time $T_4$ as the target reach time), thereby obtaining a new injection speed (injection pressure). For example, the calculator 35 sets the injection speed at time $T_5$ to 4 ml/s.

The calculator 35 outputs information representing the newly obtained injection speed to the injector 5.

Upon reception of the information representing the injection speed outputted from the parameter determining part 32, the injection controller 52 causes the injection head 51 to inject the contrast agent at the injection speed (the injection pressure). For example, in a case that the injection speed at the time $T_5$ is set to 4 ml/s, the injection controller 52 controls the injection head 51 to inject the contrast agent at the injection speed of 4 ml/s. A TDC 200 shown in FIG. 5 is obtained when the injection speed (the injection pressure) is changed and the contrast agent is injected into the subject at the changed injection speed (injection pressure).

After that, the parameter determining part 32 determines the injection speed (the injection pressure) of the contrast agent in accordance with the slope of the TDC. Thus, the medical imaging apparatus according to this embodiment performs feedback control of the injection speed of the contrast agent so that the CT value reaches the target CT value (the ending CT value E) at the target reach time ($T_4$).

For example, the differential preprocessor 33 differentiates the TDC 200 at the time $T_6$ (a TDC indicated by a solid line) by time to obtain the slope of the TDC 200 at the time $T_6$. The prediction part 34 obtains a difference (the difference of the CT values) between the ending CT value E (the target CT value) and the CT value at the time $T_6$. The prediction part 34 divides the difference of the CT values by the slope of the TDC 200 at the time $T_0$ to obtain a time (the prediction time) taken for the CT value at the time $T_0$ to reach the ending CT value E (the target CT value). The calculator 35 obtains a difference (the time to the target reach time) between the time $T_6$ and the time $T_4$ as the target reach time. The calculator 35 determines whether a time from the time $T_0$ to the target reach time ($T_4$) and the prediction time obtained by the prediction part 34 coincide with each other. In a case that the time from the time $T_6$ to the target reach time (time $T_4$) and the prediction time do not coincide with each other, the calculator 35 divides the difference of the CT values (a difference between the ending CT value E and the CT value at the time $T_0$), by the time from the time $T_6$ to the target reach time ($T_4$) (a difference between the time $T_6$ and the time $T_4$ as the target reach time), thereby obtaining a new injection speed (injection pressure). In the example shown in FIG. 5, the calculator 35 sets the injection speed at the time $T_0$ to 3.5 ml/s. The calculator 35 outputs information representing the newly obtained injection speed to the injector 5. Upon reception of the information representing the injection speed outputted from the parameter determining part 32, the injection controller 52 causes the injection head 51 to inject the contrast agent at the injection speed (injection pressure). For example, when the injection speed at the time $T_6$ is set to 3.5 ml/s, the injection controller 52 changes the injection speed from 4 ml/s to 3.5 ml/s and causes the injection head 51 to inject the contrast agent.

Thus, the medical imaging apparatus according to this embodiment performs imaging by injecting the contrast agent into the subject while changing an injection speed (an injection pressure) so that the CT value reaches the target CT value at the target reach time.

This enables imaging in a state that the contrast effect is increased by flow of the contrast agent into a site to be imaged. That is to say, a high contrast effect can be obtained by injection of the contrast agent into the subject up to an empirically obtained target CT value. This enables imaging at the timing with high contrast effect and acquisition of image data with high contrast effect. A TDC varies depending on the weights of patients, diseases and so on. The medical imaging apparatus according to this embodiment changes the injection speed of the contrast agent in accordance with the slope of the TDC, and therefore, can perform imaging in a state that the contrast effect is increased even if the speed of stain of the contrast agent varies for each patient.

In the aforementioned embodiment, the parameter determining part 32 obtains, by linear prediction, a prediction time taken for the CT value to reach the target CT value. As another example, the parameter determining part 32 may obtain the prediction time by gamma fitting of the TDC to obtain the injection speed of the contrast agent.

From the viewpoint of safety for the subject, the upper limit value of the injection speed (the injection pressure) may be determined in advance. This upper limit value is stored in advance in a storage, which is not shown in the drawing. The parameter determining part 32 may determine a new injection speed (injection pressure) up to this upper limit value and output information representing the injection speed to the injector 5.

In a case that the CT value does not reach the target CT value within a predetermined time by the target reach time even if the contrast agent is injected into the subject at the upper limit value of the injection speed (the injection pressure), injection of the contrast agent may be stopped. That is to say, the parameter determining part 32 divides a difference (the difference of the CT values) between the target CT value and the CT value at the latest time by a set injection speed, thereby obtaining a time (the prediction time) taken for the CT value at the latest time to reach the target CT value. The parameter determining part 32 compares the prediction time with the target reach time to determine whether the CT value reaches the target reach value within a certain time having been set in advance up to the target reach time. The parameter determining part 32 outputs an instruction to stop injection of the contrast agent to the injection controller 52 in a case that the CT value does not reach the target CT value within the certain time up to the target reach time. Upon reception of the stopping instruction from the parameter determining part 32, the injection controller 52 causes the injection head 51 to stop injection of the contrast agent. On the other hand, in a case that the CT value will reach the target CT value within the certain time up to the target reach time, the parameter determining part 32 does not output the aforementioned stopping instruction to the injection controller 52. As a result, the injection controller 52 causes the injection head to inject the contrast agent at a set injection speed. By thus stopping injection of the contrast agent in a case that the CT value will not reach the target CT value within the certain time up to the target reach time, it becomes possible to secure safety for the subject.

The scan controller 28, the CT value calculator 30, the second monitor 31 and the parameter determining part 32 may be each configured by a CPU (Central Processing Unit) and a storage device such as a ROM (Read Only Memory) or an HDD (Hard Disk Drive).

Either the CPU or the storage device is not shown in the drawing.

The storage device stores a scan control program for executing the function of the scan controller 28, a CT value calculation program for executing the function of the CT value calculator 30, a second monitor program for executing the function of the second monitor 31, and a parameter determination program for executing the function of the parameter determining part 32. The scan control program includes a first monitor program for executing the function of the first monitor 29.

The parameter determination program includes a differential processing program for executing the function of the differential processor 33, a prediction program for executing the function of the prediction part 34, and a calculation program for executing the function of the calculator 35. The CPU executes the respective programs to execute the functions of the respective parts.

With reference to FIG. 6, the operation of the medical imaging apparatus according to this embodiment will be described. FIG. 6 is a flow chart for describing the operation of the medical imaging apparatus according to this embodiment.

(First Operation)

A first operation will be described. In the first operation, the medical imaging apparatus according to this embodiment stops injection of the contrast agent when the CT value within the ROI becomes the stopping CT value or more.

(Step S01)

The operator inputs imaging conditions through the input part 27.

The imaging conditions include, for example, the condition of scanogram imaging for determining an imaging position, the condition of positioning imaging for setting the ROI, the prep scan condition (a tube voltage, a tube current, a scan time and so on), the main scan condition (a tube voltage, a tube current, a scan time and so on), the prep condition (the condition of start of the main scan (the threshold of the CT value)), and the stopping condition (the stopping CT value A) for stopping injection of the contrast agent. The imaging conditions are stored into a storage, which is not shown in the drawing, incorporated in the consol part 2.

(Step S02)

After the imaging conditions are set, the X-ray CT apparatus according to this embodiment executes scanogram imaging for determining an imaging position, and thereafter, executes imaging for setting the ROI.

(Step S03)

The display controller 25 causes the display 26 to display an image obtained by imaging for setting the ROI. The operator designates, through the input part 27, a region to monitor the CT value as the ROI, on the image displayed by the display 26. The region designated by the operator is set as the ROI into the CT value calculator 30. For example, through the input part 27, the operator designates the ROI to a region in which aorta is represented.

(Step S04)

The operator gives an instruction to start injection of the contrast agent to the injector 5, through the input part 27. Upon reception of the instruction to start injection of the contrast agent through the input part 27, the injection controller 52 causes the injection head 51 to inject the contrast agent in accordance with the instruction. The injection head 51 injects, for example, 100 ml of contrast agent in total into the subject at an injection speed (an injection pressure) of 3 ml/sec. Moreover, upon reception of the instruction to start injection given through the input part 27, the scan controller 28 times from the timing that the instruction is given. As one example, the scan controller 28 starts the prep scan ten seconds after the reception of the instruction to start injection of the contrast agent.

Under control by the scan controller 28, the prep scan is performed in accordance with the prep scan condition. While performing the prep scan, the scan controller 28 controls the reconstruction part 22. The reconstruction part 22 generates image data based on the X-ray projection data obtained by the prep scan.

(Step S05)

When the scan is started, the CT value calculator 30 receives the image data generated by the reconstruction part 22 and obtains the CT value within the ROI based on the image data. The CT value calculator 30 obtains the CT value within the ROI along the time series.

During execution of the prep scan, the first monitor 29 determines a point that the CT value within the ROI becomes the threshold indicated by the prep condition or more, as the timing to start the main scan. In this case, the scan controller 28 stops the prep scan and executes the main scan in accordance with the main scan condition.

For example, in a case that the threshold (the CT value) in the prep condition is set to 80 [HU], the scan controller 28 stops the prep scan and executes the main scan in accordance with the main scan condition, when the CT value within the ROI becomes 80 [HU] or more.

As one example of the main scan, the scan controller 28 executes, for 30 seconds, first intermittent imaging of executing imaging and stop imaging repeatedly for every one second. After that, the scan controller 28 executes, for 30 seconds, second intermittent imaging of executing imaging and stop imaging repeatedly for every two seconds. The first intermittent imaging is an imaging method of repeatedly executing scan while stopping scan for one second after one scan. The second intermittent imaging is an imaging method of repeatedly executing scan while stopping scan for two seconds after one scan. These imaging conditions are merely examples, and imaging may be performed under different conditions from these imaging conditions.

(Step S06)

Thus, the CT value calculator 30 obtains the CT value within the ROI, and the TDC representing a temporal change of the CT value is thereby obtained.

(Step S07)

While executing the main scan, the scan controller 28 determines whether the target reach time (the time taken for the CT value to reach the target CT value) has been set as the imaging condition.

(Step S08)

Since the target reach time has not been set in the first operation (step S07, No), the scan controller 28 controls the second monitor 31 to monitor the CT value within the ROI. The second monitor 31 receives, from the CT value calculator 30, the CT value within the ROI at each time. The second monitor 31 compares the CT value at each time with the stopping CT value A set in advance to determine whether the CT value within the ROI has become the stopping CT value A or more.

(Step S09)

When the CT value within the ROI becomes the stopping CT value A or more, the second monitor 31 outputs an instruction to stop injection of the contrast agent to the injector 5 (step S08, Yes). As one example, in a case that 300 [HU] has been set as the stopping CT value A, the second monitor 31 outputs the instruction to stop injection of the contrast agent to the injector 5 when the CT value within the ROI becomes 300 [HU] or more. Upon reception of the instruction to stop injection of the contrast agent from the second monitor 31, the injection controller 52 stops injection of the contrast agent into the subject by the injection head 51 (step S09). On the other hand, in a case that the CT value within the region of interest is less than the stopping CT value A (300 [HU]), the second monitor 31 continues monitoring the CT value within the region of interest (step S08, No).

Alternatively, instead of determining the timing of stop of injection of the contrast agent based on the stopping CT value A, the second monitor 31 may determine the timing of stop of injection of the contrast agent based on the peak of the TDC formed by the CT value within the ROI at each time. For example, the second monitor 31 differentiates the TDC by time to obtain a time when the TDC forms the peak. When detecting the peak of the TDC, the second monitor 31 outputs the instruction to stop injection of the contrast agent to the injector 5 at that point. Upon reception of the instruction to stop injection of the contrast agent from the second monitor 31, the injection controller 52 stops injection of the contrast agent into the subject by the injection head 51.

After injection of the contrast agent by the injector 5 is stopped, the scan controller 28 still executes the main scan. As one example, the scan controller 28 executes the first intermittent imaging, and thereafter, executes the second intermittent imaging.

Thus, the threshold to stop injection of the contrast agent (the stopping CT value A) is set in advance and, when the CT value within the ROI becomes the stopping CT value A or more, injection of the contrast agent is stopped. This makes it possible to reduce the wasted contrast agent while imaging in a state that the contrast agent has flown into a target site.

The second monitor 31 may output the instruction to stop injection of the contrast agent by another method. For example, the second monitor 31 obtains the slope of the TDC. The second monitor 31 obtains, based on the slope of the TDC, a time taken for the CT value within the ROI to reach the stopping CT value A. When the time is a predetermined time or more, the second monitor 31 outputs the instruction to stop injection of the contrast agent to the injector 5.

As one example, the second monitor 31 outputs the instruction to stop injection of the contrast agent in a case that it takes 30 seconds or more before the CT value within the ROI reaches the stopping CT value A. Upon reception of the stopping instruction from the second monitor 31, the injection controller 52 stops injection of the contrast agent into the subject by the injection head 51. Thus, by stopping injection of the contrast agent when the time taken for the CT value within the ROI to reach the stopping CT value A is a predetermined time or more, it is possible to secure safety for the subject.

The display controller 25 may control the display 26 to display the TDC upon reception of the CT value at each time from the CT value calculator 30. The operator may observe the TDC displayed on the display 26 to designate the timing to stop injection of the contrast agent. For example, when the TDC widely varies, injection of the contrast agent may be manually stopped.

(Second Operation)

A second operation will be described. In the second operation, the medical imaging apparatus according to this embodiment monitors the slope of the TDC and controls injection of the contrast agent so that the CT value reaches the target CT value at the target reach time.

(Step S01)

The operator inputs imaging conditions through the input part 27.

The imaging conditions include, for example, a condition of scanogram imaging for determining an imaging position, a condition of positioning imaging for setting the ROI, a prep scan condition (a tube voltage, a voltage current, a scan time and so on), a main scan condition (a tube voltage, a tube current, a scan time and so on), a prep condition (a condition of start of the main scan (a threshold of the CT value)), a CT value at the time of stopping injection of the contrast agent (the target CT value), and a required time from a point that injection of the contrast agent into the subject is started to a point that the CT value reaches the target CT value (the target reach time). The imaging condition is stored into a storage, which is not shown in the drawing, incorporated in the console part 2.

(Step S02)

After the imaging conditions are set, the X-ray CT apparatus according to this embodiment executes scanogram imaging for determining an imaging position, and thereafter, executes imaging for setting the ROI.

(Step S03)

The display controller 25 controls the display 26 to display an image obtained by the imaging for setting the ROI. Through the input part 27, the operator designates a region to monitor the CT value as the ROI on the image displayed by the display 26. The region designated by the operator is set as the ROI into the CT value calculator 30. For example, the operator sets a region representing aorta as the ROI through the input part 27.

(Step S04)

The operator gives an instruction to start injection of the contrast agent to the injector 5 through the input part 27. Upon reception of the instruction to start injection of the contrast agent through the input part 27, the injection controller 52 controls the injection head 51 to inject the contrast agent in accordance with the instruction. The injection head 51 injects 100 ml of contrast agent in total as the initial value into the subject at an injection speed (an injection pressure) of 3 ml/sec. Moreover, upon reception of the instruction to start injection given through the input part 27, the scan controller 28 times from the timing that the instruction is given. As one example, the scan controller 28 starts the prep scan after a lapse of ten seconds from reception of the instruction to start injection of the contrast agent. Under control by the scan controller 28, the prep scan is performed in accordance with the prep scan condition. While performing the prep scan, the scan controller 28 controls the reconstruction processor 22. The reconstruction processor 22 generates image data based on the X-ray projection data obtained by the prep scan.

(Step S05)

When the scan is started, the CT value calculator 30 receives the image data generated by the reconstruction processor 22 and obtains the CT value within the ROI based on the image data. The CT value calculator 30 obtains the CT value within the ROI along the time series.

During execution of the prep scan, the first monitor 29 determines a point that the CT value within the ROI becomes the threshold represented by the prep condition or more, as the timing of start of the main scan. In this case, the scan controller 28 stops the prep scan and executes the main scan in accordance with the main scan condition. For example, in a case that 80 [HU] is set as the threshold (the CT value) in the prep condition, the scan controller 28 stops the prep scan and executes the main scan in accordance with the main scan condition when the CT value within the ROI becomes 80 [HU] or more.

As described above, as one example, the scan controller 28 executes the first intermittent imaging for 30 seconds, and thereafter, executes the second intermittent imaging for 30 seconds.

(Step S06)

Thus, the CT value calculator 30 obtains the CT value within the ROI, and the TDC representing a temporal change of the CT value is thereby obtained.

(Step S07)

While executing the main scan, the scan controller 28 determines whether the target reach time (a time taken for the CT value to reach the target CT value) has been set as the imaging condition.

(Step S10)

Since the target reach time has been set in the second operation (step S07, Yes), the scan controller 28 controls the parameter determining part 32 to obtain the injection speed of the contrast agent.

The differential processor 33 receives the CT value within the ROI at each time from the CT value calculator 30 and differentiates the TDC with respect to time, thereby obtaining the slope of the TDC at each time.

(Step S11)

Upon reception of the slope of the TDC at each time obtained by the differential processor 33, the prediction part 34 obtains a difference between the target CT value and the CT value at the latest time (the difference of the CT values). The prediction part 34 divides the difference of the CT values by the slope of the TDC at the latest time to obtain a time (the prediction time) to reach the target CT value from the CT value at the latest time.

(Step S12)

The calculator 35 obtains a difference (the time to the target reach time) between the aforementioned latest time and the target reach time. The calculator 35 determines whether the time to the target reach time and the prediction time obtained by the prediction part 34 coincide with each other.

(Step S13)

In a case that the time to the target reach time and the prediction time coincide with each other (step S12, Yes), it is predicted that, by injection of the contrast agent in accordance with the set injection speed (3 ml/sec), the CT value will reach the target CT value at the target reach time. In this case, the injection controller 52 controls the injection head 51 to inject the contrast agent at the set injection speed (3 ml/sec) without changing the injection speed of the contrast agent.

The scan controller 28 controls the second monitor 31 to monitor the CT value within the ROI. Upon reception of the CT value within the ROI at each time from the CT value calculator 30, the second monitor 31 compares the CT value at each time with the target CT value set in advance to determine whether the CT value within the ROI has become the target CT value. When the CT value within the ROI has become the target CT value, the second monitor 31 outputs an instruction to stop injection of the contrast agent to the injector 5 (step S13, Yes). As one example, in a case that 300 [HU] is set as the target CT value, the second monitor 31 outputs the instruction to stop injection of the contrast agent to the injector 5 when the CT value within the ROI becomes 300 [HU] or more. Upon reception of the instruction to stop injection of the contrast agent from the second monitor 31, the injection controller 52 stops injection of the contrast agent into the subject by the injection head 51 (step S09). On the other hand, the second monitor 31 continuously monitors the CT value within the ROI when the CT value within the ROI is less than the target CT value (300 [HU]).

(Step S12, Step S14)

When the time to the target reach time and the prediction time do not coincide with each other, it is predicted at step S12 that the CT value will not reach the target CT value at the target reach time even if the contrast agent is injected in accordance with the set injection speed (step S12, No). In this case, the calculator 35 divides the aforementioned difference of the CT values by the aforementioned time to the target reach time, thereby obtaining a new injection speed (injection pressure). Thus, the calculator 35 obtains an injection speed of the contrast agent for the CT value to reach the target CT value at the target reach time. The calculator 35 outputs information representing the newly obtained injection speed to the injector 5. Upon reception of the information representing the injection speed outputted from the parameter determining part 32, the injection controller 52 controls the injection head 51 to inject the contrast agent at the injection speed. For example, the injection controller 52 changes the injection speed from 3 ml/sec of the initial value to 4 ml/sec and controls the injection head 51 to inject the contrast agent.

After that, the medical imaging apparatus according to this embodiment repeatedly executes the process from step S10 to step S12 and, when the CT value becomes the target CT value, stops injection of the contrast agent.

At step S12, the calculator 35 may determine whether a difference between the time to the target reach time and the prediction time is less than a certain time having been set in advance. In a case that the difference between the time to the target reach time and the prediction time is less than the certain time, it is predicted that injection of the contrast agent in accordance with the set injection speed (3 ml/sec) will cause the CT value to reach substantially the target CT value at the target reach time. In this case, the injection controller 52 controls the injection head 51 to inject the contrast agent at the set injection speed (3 ml/sec) without changing the injection speed of the contrast agent.

At step S12, in a case that the difference between the time to the target reach time and the prediction time is equal to or more than the certain time, it is predicted that injection of the contrast agent at the set injection speed will not cause the CT value to reach substantially the target CT value at the target reach time. In this case, the calculator 35 divides the aforementioned difference of the CT values by the aforementioned time to the target reach time, thereby obtaining a new injection speed. The predetermined time is prestored in a storage, which is not shown in the drawing, incorporated in the console part 2.

Thus, by injecting the contrast agent into the subject while changing the injection speed so that the CT value reaches the target CT value at the target reach time, it is possible to perform imaging in a condition that the contrast effect is increased. For example, the TDC largely varies depending on the weight, disease and so on of a patient.

The medical imaging apparatus according to this embodiment changes the injection speed of the contrast agent in accordance with the slope of the TDC, and is therefore capable of performing imaging with the contrast effect increased even if the speed of stain of the contrast agent varies for each patient.

This embodiment has described a case that the prep scan is executed. As another example, it is possible to produce the effect of the medical imaging apparatus according to this embodiment without executing the prep scan. For example, a dynamic scan of repeatedly radiating a subject with an X-ray may be executed to generate a plurality of image data.

What is claimed is:

1. A medical imaging apparatus, comprising:
a processor configured to cause an X-ray source and detector to image a subject with a contrast agent injected, and acquire a plurality of image data of the subject respectively at different times;
a pixel value calculator configured to obtain, for each image data of the plurality of image data, a pixel value for the image data; and
an injection controller configured to control injection of the contrast agent by an injector configured to inject a contrast agent into a subject in accordance with each pixel value obtained by the pixel value calculator,
wherein the injection controller is further configured to stop injection of the contrast agent by the injector when one of the pixel values obtained by the pixel value calculator becomes at least a preset stopping threshold.

2. The medical imaging apparatus according to claim 1, wherein the injection controller is further configured to control injection of the contrast agent by the injector in proportion to a temporal change rate of the pixel values.

3. The medical imaging apparatus according to claim 1, wherein the injection controller is further configured to stop injection of the contrast agent by the injector after a temporal change rate of the pixel values reaches a peak.

4. The medical imaging apparatus according to claim 1, wherein the injection controller is further configured to control the injection part to inject the contrast agent while changing the injection speed so that at least one of the pixel values reaches a target pixel value at a target reach time after a lapse of a predetermined time from a start of injection of the contrast agent by the injector.

5. The medical imaging apparatus according to claim 4, wherein the processor is further configured to obtain a pixel value difference between a new pixel value within a region of interest in new image data acquired by the processor and the target pixel value, obtain a temporal difference between a point of acquisition of the new image data and the target reach time, and divide the pixel value difference by the temporal difference to obtain a new injection speed,
wherein the injection controller is configured to control the injector to inject the contrast agent in accordance with the new injection speed.

6. The medical imaging apparatus according to claim 5, wherein the processor is further configured to obtain a temporal change rate of the pixel values, obtain a prediction time taken for one of the pixel values to reach the target pixel value using the temporal change rate, and obtain the new injection speed when a difference between the prediction time and the temporal difference exceeds a threshold.

7. The medical imaging apparatus according to claim 1, wherein the processor is further configured to cause the X-ray source to repeatedly radiate the subject, with the contrast agent injected, with an X-ray to acquire the plurality of image data.

8. The medical imaging apparatus of claim 1, wherein the pixel value calculator is configured to obtain the pixel value from a region of interest set in the image data.

9. A medical imaging method, comprising:
injecting a contrast agent into a subject at a predetermined injection speed;
imaging the subject with the contrast agent injected to acquire a plurality of image data of the subject respectively at different times;
obtaining, for each image data of the plurality of image data, a pixel value for the image data, the pixel value being obtained from a region of interest set in the image data; and
controlling injection of the contrast agent in accordance with each pixel value obtained in the obtaining step,
wherein the controlling step includes stopping injection of the contrast agent when one of the pixel values obtained in the obtaining step becomes at least a preset stopping threshold.

10. The medical imaging method according to claim 9, wherein injection of the contrast agent is further controlled in proportion to a temporal change rate of the pixel values.

11. The medical imaging method according to claim 9, wherein injection of the contrast agent is stopped after a temporal change rate of the pixel values reaches a peak.

12. The medical imaging method according to claim 9, wherein the contrast agent is injected into the subject while the injection speed is changed so that at least one of the pixel values reaches a target pixel value at a target reach time after a lapse of a predetermined time from a start of injection of the contrast agent.

13. The medical imaging method according to claim 12, further comprising:
obtaining a pixel value difference between a new pixel value within the region of interest in new acquired image data and the target pixel value,
obtaining a temporal difference between a point of acquisition of the new image data and the target reach time, and
dividing the pixel value difference by the temporal difference to obtain a new injection speed, wherein the contrast agent is injected into the subject in accordance with the new injection speed.

14. The medical imaging method according to claim 13, wherein a temporal change rate of the pixel values is obtained, a prediction time taken for one of the pixel values to reach the target pixel value is obtained using the temporal change rate, and the new injection speed is obtained when a difference between the prediction time and the temporal difference exceeds a threshold.

15. The medical imaging method to claim 9, wherein the imaging step includes repeatedly radiating the subject, with the contrast agent injected, with an X-ray to acquire the plurality of image data.

* * * * *